ically selected from the group consisting
United States Patent
Dighe et al.

[11] 3,959,366
[45] May 25, 1976

[54] POLYENES FROM DIPHENYL ETHERS
[75] Inventors: Shrikant V. Dighe, Silver Spring; Richard W. Bush, Columbia, both of Md.
[73] Assignee: W. R. Grace & Co., New York, N.Y.
[22] Filed: June 24, 1974
[21] Appl. No.: 482,735

Related U.S. Application Data
[62] Division of Ser. No. 303,848, Nov. 6, 1972, Pat. No. 3,856,858.

[52] U.S. Cl. .................... 260/543 R; 260/556 AR
[51] Int. Cl.² ................ C07C 143/78; C07C 143/79
[58] Field of Search .................... 260/543 R, 543 F

[56] References Cited
UNITED STATES PATENTS
3,639,469  2/1972  Suzuki .......................... 260/543 R Primary Examiner—Vivian Garner
Attorney, Agent, or Firm—Elton Fisher

[57] ABSTRACT
The compound:

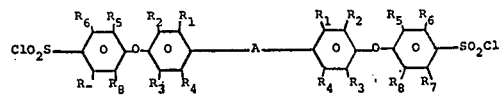

which can be reacted with dialkylamine to form a product compound having the formula

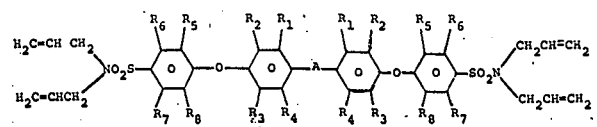

in which:
a. $R_1$, $R_2$, $R_3$, $R_4$, $R_5$, $R_6$, $R_7$, and $R_8$ are independently selected from the group consisting of hydrogen, fluorine, chloride, bromine, and lower alkyl;

b. A is   A is $SO_2-\overset{R_{10}}{\underset{|}{N}}-R_9-\overset{R_{11}}{\underset{|}{N}}-O_2S$ ;

c. $R_9$ is

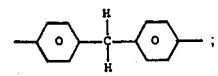

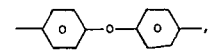

an alkylene group having 2–20 carbon atoms, a cycloalkylene group having 3–20 carbon atoms, a phenylene group, an alkaryl group having 7–10 carbon atoms, or an aralkyl group having 7–10 carbon atoms; and d. $R_{10}$ and $R_{11}$ are independently selected from a group consisting of hydrogen, lower alkyl, a cycloalkyl group having 3–10 carbon aboms, a phenyl group, an alkylaryl group having 7–10 carbon atoms, and an aralkyl group having 7–10 carbon atoms. The product compound can be admixed with a polythiol to form a composition which is useful for (a) preparing printing plates and (b) protective coatings

4 Claims, No Drawings

POLYENES FROM DIPHENYL ETHERS

This is a division of application Ser. No. 308,848, filed Nov. 6, 1972, now U.S. Pat. No. 3,856,858.

BACKGROUND OF THE INVENTION

This invention is directed to; (a) N,N,N'N'-tetrallyl-diphenylether-4,4'-disulfonamide (TADEDS); (b) a number of related sulfonamides; and (c) the preparation of such sulfonamides from diphenylether-4,4'-disulfonyl chloride (DEDSC) or nuclear substituted DEDSC and diallylamine. DEDSC is commercially available from National Polychemicals, Inc., Wilmington, Mass., and 4,4'-disulfonyl chlorides of substituted diphenylethers can be readily prepared by obvious conventional methods including those recited hereinafter.

SUMMARY OF THE INVENTION

In summary this invention is directed to a compound having the formula

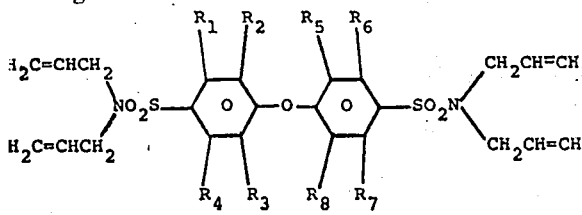

in which $R_1$, $R_2$, $R_3$, $R_4$, $R_5$, $R_6$, $R_7$, and $R_8$ are independently selected from the group consisting of hydrogen, fluorine, chlorine, bromine, and lower alkyl.

DESCRIPTION OF THE PREFERRED EMBODIMENTS

In a preferred embodiment of the compound of the above Summary $R_1$, $R_2$, $R_3$, $R_4$, $R_5$, $R_6$, $R_7$, and $R_8$ are hydrogen.

In another preferred embodiment (Embodiment A) this invention is directed to a compound having the formula

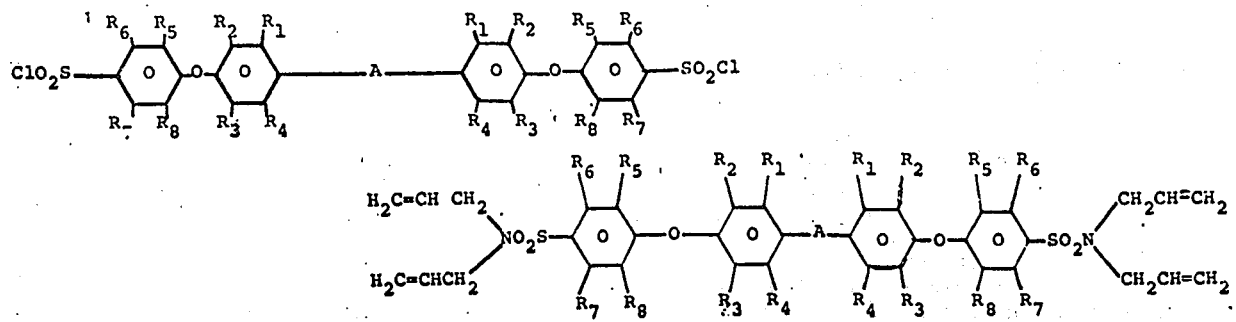

in which:
a. $R_2$, $R_3$, $R_4$, $R_5$, $R_6$, $R_7$, and $R_8$ are independently selected from the group consisting of hydrogen, fluorine, chloride, bromine, and lower alkyl;
b. A is $$-SO_2-N-R_9-N-O_2S-$$
with $R_{10}$, $R_{11}$ substituents c. $R_9$ is

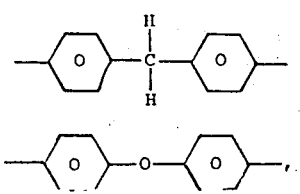

an alkylene group having 2–20 carbon atoms, a cycloalkylene group having 3–10 carbon atoms, a phenylene group, an alkaryl group having 7–10 carbon atoms, or an aralkyl group having 7–10 carbon atoms; and d. $R_{10}$ and $R_{11}$ are independently selected from a a group consisting of hydrogen, lower alkyl, a cycloalkyl group having 3–10 carbon atoms, a phenyl group, an alkylaryl group having 7–10 carbon atoms, and an aralkyl group having 7–10 carbon atoms.

In specially preferred embodiments of the compound of Embodiment A, supra:

1. $R_1$, $R_2$, $R_3$, $R_4$, $R_5$, $R_6$, $R_7$, $R_8$, $R_{10}$, and $R_{11}$ are hydrogen.
2. $R_1$, $R_2$, $R_3$, $R_4$, $R_5$, $R_6$, $R_7$, and $R_8$ (i.e., $R_1$ through $R_8$) are hydrogen and $R_9$ is

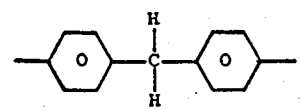

3. $R_1$ through $R_8$ are hydrogen, $R_{10}$ and 11 are hydrogen, and $R_9$ is

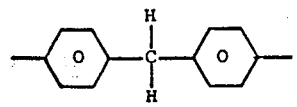

4. $R_1$ through $R_8$ are hydrogen and $R_9$ is an alkylene group having about 2–12 carbon atoms.
5. $R_1$ through $R_8$ are hydogen and $R_9$ is $-CH_2(CH_2)_4CH_2-$.
6. $R_1$ through $R_8$ are hydrogen, $R_9$ is $-CH_2(CH_2)_4CH_2-$, and $R_{10}$ and $R_{11}$ are hydrogen.

In another preferred embodiment (Embodiment B) this invention is directed to a compound having the formula in which:
a. $R_1$, $R_2$, $R_3$, $R_4$, $R_5$, $R_6$, $R_7$, and $R_8$ are independently selected from the group consisting of hydrogen, fluorine, chloride, bromine, and lower alkyl;
b. A is $$SO_2-N-R_9-N-O_2S\ ;$$

c. $R_9$ is

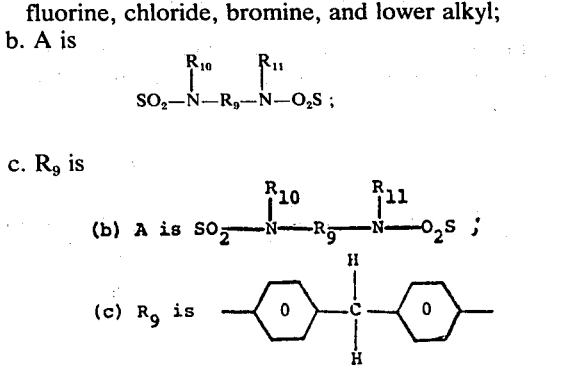

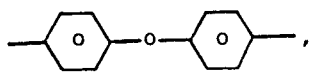

an alkylene group having 2–20 carbon atoms, a cycloalkylene group having 3–10 carbon atoms, a phenylene group, an alkaryl group having 7–10 carbon atoms, or an aralkyl group having 7–10 carbon atoms; and d. $R_{10}$ and $R_{11}$ are independently selected from a group consisting of hydrogen, lower alkyl, a cycloalkyl group having 3–10 carbon atoms, a phenyl group, an alkylaryl group having 7–10 carbon atoms, and an aralkyl group having 7–10 carbon atoms.

In specially preferred embodiments of the compound of Embodiment B, supra:

1. $R_1$ through $R_8$ are hydrogen.
2. $R_1$ through $R_8$ are hydrogen, $R_9$ is

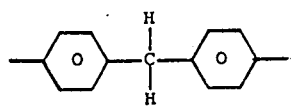

3. $R_1$ through $R_8$ are hydrogen, $R_9$ is

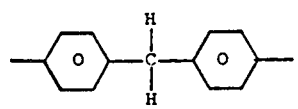

and $R_{10}$ and $R_{11}$ are hydrogen.
4. $R_1$ through $R_8$ are hydrogen and $R_9$ is an alkylene group having about 2–12 carbon atoms.
5. $R_1$ through $R_8$ are hydrogen and $R_9$ is $-CH_2(CH_2)_4CH_2-$.
6. $R_1$ through $R_8$ are hydrogen; $R_9$ is $-CH_2(CH_2)_4CH_2-$, and $R_{10}$ and $R_{11}$ are hydrogen.

In another preferred embodiment ("Embodiment C") this invention is directed to a compound having the formula

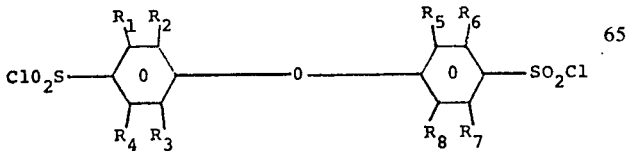

in which $R_1$, $R_2$, $R_3$, $R_4$, $R_5$, $R_6$, $R_7$, and $R_8$ are independently selected from the group consisting of hydrogen, fluorine, chlorine, bromine, and lower alkyl group provided that at least 1 of $R_1$ through $R_8$ is a group other than hydrogen.

In as especially preferred embodiment of the compound of Embodiment C, each of $R_1$ through $R_8$ is $-CH_3$.

In another preferred embodiment ("Embodiment D") this invention is directed to a curable composition consisting essentially of an intimate of; (A) a compound having the formula; (1)

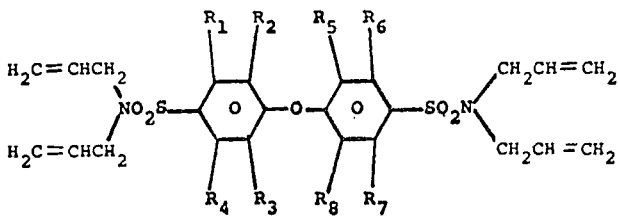

in which $R_1$, $R_2$, $R_3$, $R_4$, $R_5$, $R_6$, $R_7$, and $R_8$ are independently selected fom the group consisting of hydrogen, fluorine, chlorine, bromine, and lower alkyl; or (2)

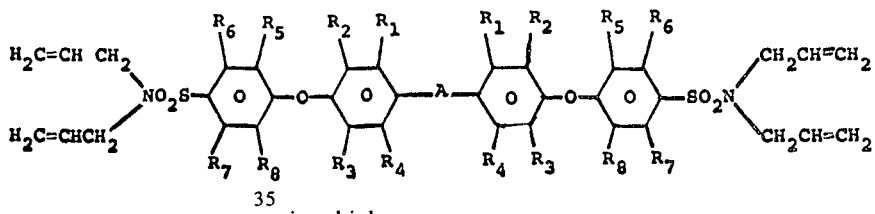

in which:

a. $R_1$, $R_2$, $R_3$, $R_4$, $R_5$, $R_6$, $R_7$, and $R_8$ are independently selected from the group consisting of hydrogen, fluorine, chloride, bromine, and lower alkyl;
b. A is

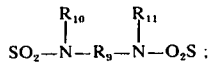

a. $R_9$ is

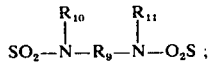

a. $R_9$ is

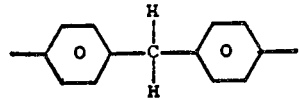

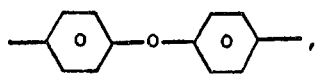

an alkylene group having 2–20 carbon atoms, a cycloalkylene group having 3–10 carbon atoms, a phenylene group, an alkaryl group having 7–10 carbon atoms, or an aralkyl group having 7–10 carbon atoms; and d. $R_{10}$ and $R_{11}$ are independently selected from a geoup consisting of hydrogen, lower alkyl, a cycloalkyl group having 3–10 carbon atoms, a phenyl group, an alkylaryl group having 7–10 carbon atoms, and an aralkyl group having 7–10 carbon atoms; and B. a liquid polythiol component having molecules containing at least two thiol groups per molecule.

In especially preferred embodiments of the composition of Embodiment D:
1. The curable composition contains a photocuring rate accelerator.
2. The photocurable rate accelerator is selected from the group consisting of aryl aldehyde, diaryl ketone, triaryl phosphine, and a blend of a carbon tetrahalide with a polynuclear aromatic hydrocarbon.
3. The photocuring rate accelerator is present in an effective amount from about 0.05 to about 25 percent by weight of the curable composition.
4. The composition contains a member of the group consisting of a filler, pigment, odor mask, light-scattering agent, plasticizer and anitoxidant in an effective amount equal to about 0.005 to about 500 parts per 100 parts of the photocurable composition.

DETAILED DESCRIPTION OF THE INVENTION

The reaction of primary and secondary amines with benzenesulfonyl chloride is well known to those skilled in the art and was used by Hinsberg to separate mixtures of primary, secondary, and tertiary amines. See; (a) Reynold C. Fuson, "Organic Chemistry," Edwards Brothers, Inc., Ann Arbor, Michigan, 1939, pp. 216–217; and (b) Ralph G. Shriner et al, "The Systematic Identification of Organic Compounds", John Wiley & Sons, Inc., New York, N.Y., 1956, pp. 103.

We have found that a modification of this reaction can be used to prepare polyenes having the formulas set forth in the above Summary and in Embodiment B, supra, and in the embodiments (number 1–6) listed under said Embodiment B which can then be reacted with a polythiol of the type taught, described, and used in U.S. Pat. Nos. 3,535,193 (161/88, R. W. Prince) and 3,578,614 (260/13, W. R. Wszolek) to prepare offset printing blankets and curable compositions (useful as adhesives and for coating surfaces (e.g., wooden surfaces, soft metal surfaces, and the like) to provide a coating which, after curing will protect the coated surfaces from the action of solvents, scratching, and the like.

We have also found that a modification of this reaction can be used to prepare compounds having the formulas set forth in Embodiment A, supra, and in the embodiments (the embodiments number 1–6) listed under said Embodiment A.

The instant invention will be better understood by referring to the following specific but nonlimiting examples. It is understood that said invention is not limited by these examples which are offered merely as ilustrations; it is also understood that modifications can be made without departing from the spirit and scope of the invention.

Example 1

Materials:

36.7 g (0.1 mole), Diphenyl ether-4,4'-disulfonyl chloride
8.0 g (0.2 mole), Sodium hydroxide
20.0 g (0.2 mole), Diallylamine In a 500 ml., three-necked round bottom flask equipped with a reflux condenser, thermometer, addition funnel and a mechanically driven stirrer were placed 8.0 g of sodium hydroxide dissolved in 100 ml of water and 20.0 g of diallylamine. The resulting mixture was heated to 50°C while stirring. Diphenyl ether disulfonyl chloride (DEDSC) dissolved in 200 ml. of tetrahydrofuran was added dropwise from the funnel. After a few ml. of the solution had been added, the temperature rose to 55°C. At this point heating was stopped and the rate of addition so adjusted as to maintain a temperature of 50°–55°C during addition. After the addition was complete, the reaction mixture was refluxed for 4 hours and then allowed to cool to room temperature. The cold solution separated into two layers. It was added to a large excess (ca. 1 liter) of water with vigorous stirring. A white precipitate separated; said precipitate was collected on a filter and dried in vacuo at 50°C. The thus dried material was recrystallized from tetrahydrofuran-pentane mixture.

The white recrystallized product melted sharply at 85°–86°C and weighed 42.5 g corresponding to a conversion (1 pass yield of 88% of theory). Said recrystalized product was identified as TADEDS by NMR (nuclear magnetic resonance).

Example 2

A composition was prepared by admixing TADEDS prepared as in Example 1, supra, with pentaerythritol tetrakis (3-mercaptopropionate) which is also known as pentaerythritol tetrakis ($\beta$-mercaptopropionate) in a mole ratio of 1:1 and incorporating into said mixture 2% by weight of benzophenone (based on the weight of the TADEDS). The resulting mixture was melted, admixed thoroughly, and spread over a thin metal sheet to form a thin film (ca. 15–20 mil thick). The resulting film was cooled to room temperature and exposed to the light of a 4,000 watt Ascorlux pulsed xenon arc printing lamp through a photographic negative having an image thereon. Exposure time was 2.6 minutes, the xenon light being about 30 inches from the surface of the aforesaid resulting film. A cured image was present on the exposed areas of said resulting film when said resulting film was developed by washing with a suitable solvent (a mixture of acetone and water in a weight ratio of about 3 parts acetone per part of water). The unexposed portions of said resulting film were dissolved and washed away by the solvent while the exposed portions of said resulting film were not dissolved (and not washed away) by said solvent. The resulting printing plate was mounted on a printing press using double-face pressure-sensitive tape and printing was carried out in the same way conventional metal photoengraved plates are employed. The printing results obatined were superior to those with conventionl plates.

Example 3

The general procedure of Example 2 was repeated, however, in this instance the procedure was modified by dissolving the resulting mixture of TADEDS, pentaerythritol tetrakis (3-mercaptopropionate) and benzophenone (after said resulting mixture had been melted and cooled) in acetone, applying a film of said acetone solution to a thin sheet of metal, and drying said film of acetone solution (i.e., freeing said film of its acetone) to form a resulting film of the composition of Example 2, (TADEDS plus pentaerythritol tetrakis (3-mercaptopropionate) plus benzophenone) having a thickness of about 15 mils on the surface of the metal sheet.

When this film of said composition was exposed to actinic light from the Xenon arc printing lamp (said light passing through a photographic negative as in Example 2) and developed as in Example 2. The resulting printing plate was mounted on a printing press using double-face pressure-sensitive tape and printing was carried out in the same way conventional metal photoengraved plates are employed. The printing results obtained were superior to those with conventional plates.

Example 4

TADEDS (N,N,N',N'-tetrallyldiphenylether-4,4'-disulfonamide) made by the procedure of Example 1 was admixed with pentaerythritol tetrakis (3-mercaptopropionate) in a mole ratio of 1:1 and 3% of benzophenone (based on the weight of the TADEDS) was added to the mixture which was then melted, admixed thoroughly, cooled to room temperature, and designated "Composition 4".

Composition 4 was dissolved in acetone and the resulting solution was designated "Composition 4-A".

Composition 4-A was coated on a fine-count laminated offset blanket carcass composed of 3 layers of square weave 80 × 80 prestretched cotton fabric impregnated and adhered together with a butadiene-acrylonitrile combining compound. Lamination of the carcass took place under heat and pressure. The carcass was coated on a spreading apparatus equipped with a movable doctor blade which ran over the surface to be coated. The coated material was immobile on the support table. After the sheet was coated, the doctor blade was moved out of the way, and the coating was dried (i.e., the acetone was evaporated therefrom). A dry (substantially acetone free) coating having a thickness of 0.020 inch resulted. The thus formed dry coating was exposed to the light of a 4,000 watt Ascorlux pulsed xenon arc printing lamp made by the American Speed Light Corp. which was placed 30 inches above the surface. Total exposure given to all portions of the coated blanket was 2 minutes and 40 seconds, the actinic light having passed through a photographic negative. The thus exposed coating was developed by treating with a mixture of acetone and water to remove uncured material and to form a fully devleoped offset plate. Thereafter the blanket was removed from the apparatus, punched at either end to receive blanket hooks and wrapped around the cylinder of a small offset printing press. The lithograph plate test copy was prepared with 11 densities ranging from full black to light gray. Each density was properly reproduced. Performance in all respects equaled a conventionally coated offset blanket.

Example 5

Materials:

36.7 g (0.1 mole) DEDSC
4.0 g (0.1 mole) Sodium hydroxide
9.9 g (0.05 mole) Methylene bis-aniline In a 1-liter, three-necked, round bottom flask equipped with a condenser, thermometer, addition funnel, and a mechanically driven stirrer were placed 4.0 g of sodium hydroxide dissolved in 100 ml. of water and 9.9 g of methylene bis-aniline dissolved in 100 ml. tetrahydrofuran. The stirred mixture was heated to 50°C and a solution of 36.7 g DEDSC in 100 ml. tetrahydrofuran added dropwise at such a rate as to maintain a reaction temperature of 50°–55°C. After the addition was complete, the reaction mixture was refluxed for one hour and allowed to cool to room temperature. The cooled mixture was designated "Mixture 5-A".

A small sample of the cooled mixture (Mixture 5-A) was removed from the reaction flask, evaporated to dryness (i.e., until substantially free of solvent) under reduced pressure leaving a first residue. The first residue was extracted wih a small quantity of dilute (ca. 2 molar) aqueous hydrochloric acid solution, leaving an extracted residue behind. The extracted residue was dried under reduced pressure leaving a second residue behind. This second residue was identified by NMR and by its infrared spectrum as

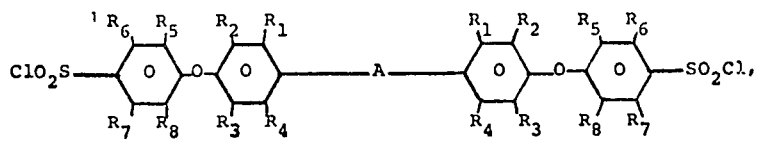

in which; (a) $R_1$ through $R_8$ are hydrogen; (b) A is

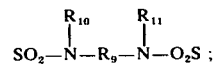

c. $R_9$ is

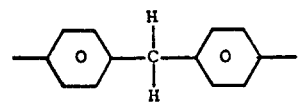

and (d) $R_{10}$ and $R_{11}$ are hydrogen.

A solution of (4 g in 50 ml of water) was added to Mixture 5-A in the reaction flask and the resulting mixture was reheated to 60°C. Diallylamine (9.8 g, 0.1 mole) was added dropwise and the mixture was added to a large excess of water. A pale brown, clear solution resulted. On acidification a white-brown precipitate was obtained. This precipitate was dried (freed of solvent) under reduced pressure. The dried precipitate, which was designated "Product 5-B", was identified by NMR and by its infrared spectrum as

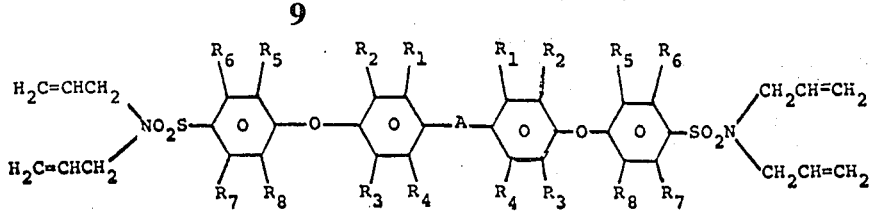

in which; (a) $R_1$ through $R_8$ were hydrogen; (b) A was

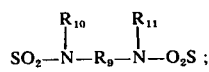

(c) $R_9$ was

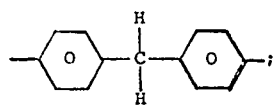

and (d) $R_{10}$ and $R_{11}$ were hydrogen.

Example 6

The general procedure of Example 4, supra, was repeated. However, in this instance, the TADEDS used in Example 4 was replaced with Product 5-B (from Example 5, supra). The results obtained were indistinguishable from those of Example 4.

Example 7

Materials: 36.7g (0.1 mole) DEDSC
9.3g (0.08 mole) Hexamethylenediamine
3.2g (0.08 mole) Sodium Hydroxide In a 1-liter, three-necked, round bottom flask equipped with a condenser, thermometer, addition funnel, and a mechanically driven stirrer were placed 9.3 g of hexamethylenediamine dissolved in 100 ml of tetrahydrofuran and 3.2 g of sodium hydoxide dissolved in 100 ml of water. The stirred mixture was heated to 50°–55°C. and 3.6 g of DEDSC dissolved in 100 ml of tetrahydrofuran was added dropwise to maintain the reaction temperature at 55°–60°C. After the addition was complete, the reaction mixture was refluxed for one hour and allowed to cool to room temperature. The cooled mixture was designated "Mixture 7-A".

A small sample of the cooled mixture (Mixture 7-A) was removed from the reaction flask, evaporated to dryness (i.e., until substantially free of solvent) under reduced pressure leaving a first residue. The first residue was extracted with a small quantity of dilute (ca. 2molar) aqueous hydrochloric acid solution leaving an extracted residue behind. The extracted residue was dried under reduced pressure leaving a dried residue behind. This dried residue was identified by NMR and by its infrared spectrum as in which; (a) $R_1$ through $R_8$ are hydrogen (b) A is

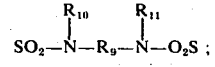

c. $R_9$ is $-CH_2(CH_2)_4CH_2-$; and (d) $R_{10}$ and $R_{11}$ are hydrogen.

A solution of 1.6 g (0.04 mole) of sodium hydroxide in 50 ml of water was added to Mixture 7-A in the reaction flask. The resulting mixture in said flask was heated to 55°–60°C. Diallylamine (4 g, 0.04 mole) was added dropwise and the resulting reaction mixture refluxed for an hour, cooled to room temperature, added to 500 ml of water, and acidified with hydrochloric acid to pH 5–6 causing a white precipitate to form. The precipitate was separated by fiteration and dried under reduced pressure. The thus dried precipitate, which was designated "Product 7-B" was identified by NMR and by its infrared spectrum as

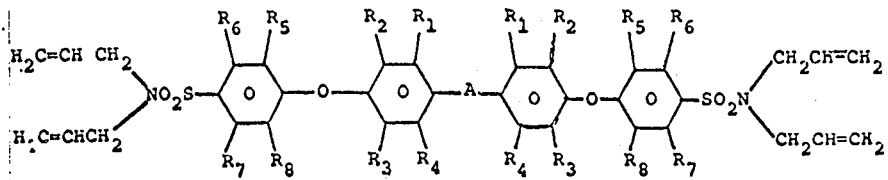

in which; (a) $R_1$ through $R_8$ were hydrogen; (b) A was

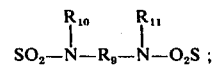

c. $R_9$ is $-CH_2(CH_2)_4CH_2-$; and (d) $R_{10}$ and $R_{11}$ were hydrogen.

Example 8

The general procedure of Example 4 was repeated. However, in this instance, the TADEDS of Example 4, supra, was replaced with Product 7-B (from Example 7, supra). The results were indistinguishable from those of Example 4.

Example 9

Run No. 1: Preparation of Compound 9-A, said compound having the formula

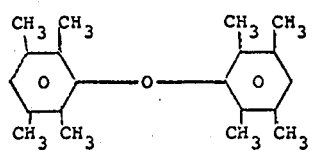

Several batches of the above-identified Compound

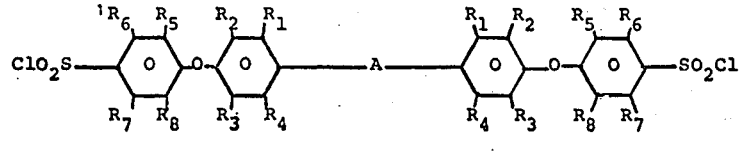

9-A were prepared by:
1. Admixing 0.25 mole of 2,3,5,6-tetramethylphenol and 1 mole of NaOH (present as an aqueous solution analyzing about 36% NaOH) in a reaction flask having a reflux condenser, an entrance port, and a mechanically driven stirrer. Water was added as necessary to place the phenol in solution.
2. Adding 0.25 mole of 1-bromo-2,3,5,6-tetramethylbenzene to the first mixture while stirring the resulting second mixture and heating said second mixture to maintain a vigorous reflux-after refluxing for about 2 hours the second mixture was cooled to about 25°C.
3. A third mixture was formed by neutralizing the cooled second mixture with dilute hydrochloric acid (ca. 6 normal) using litmus paper as indicator. The third mixture was cooled to about 15°C.
4. The cooled third mixture was extracted with one half its volume of cool (ca. 15°C.) ether (i.e., ethyl ether ($C_2H_5OC_2H_5$)); the thus extracted third mixture was extraced with a second portion of cool ether, and the 2 portions of ether extract were combined and washed with cool water (ca. 15°C.) using about one volume of water per 5 volumes of ether extract. The thus washed ether extract was dried with Drierite (anhydrous calcium sulfate). The resulting dried ether extract—a solution of Compound 9-A in ether—was designated "Fourth Mixture".
5. Said compound 9-A was recovered from the fourth mixture by distilling the ethyl ether from the fourth mixture.

Compound 9-A was characterized and identified by elemental analysis and by its nuclear magnetic resonance (NMR) and infrared spectra.

Run No. 2; Compound 9-A was converted to Compound 9-B, said Compound 9-B having the formula

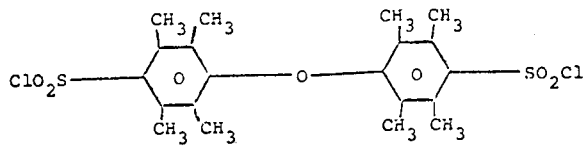

by reaction of the above-described compound 9-A with chlorosulfonic acid by slowly adding 0.2 mole said Compound 9-A to 1 mole of cold (ca. 0°C.) chlorosulfonic acid while stirring the resulting mixture and maintaining it at about 0°C. The resulting mixture was maintained at about 0°C. for about 3 hours and then poured over a kilogram of crushed ice. The resulting Compound 9-B separated out. The separated Compound 9-B was recovered and dried under vacuum at about 50°C. Compound 9-B was characterized and identified by elemental analysis and by its NMR and infrared spectra.

Run No. 3: The general procedure of Runs Nos. 1 and 2 of this Example were repeated. However, in this instance, the procedure used in Run No. 2 was modified by replacing the chlorosulfonic acid with a mixture of 1 mole of fuming sulfuric acid (ca. 10% free $SO_3$ content) and 1 mole of $PCl_5$. The resulting product (Compound 9-B) was recovered, dried, and identified as in said Run No. 2.

Run No. 4: The general procedure of Example 1 was repeated. However, in this instance the procedure was modified by replacing the DEDSC of Example 1 with Compound 9-B from Run No. 2 of Example 9. The product "Compound 9-C" was identified by elemental analysis, NMR, and its infrared spectrum as

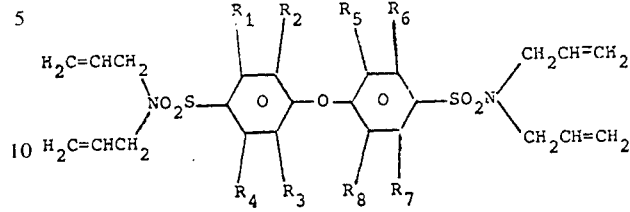

in which $R_1$ through $R_8$ were each —$CH_3$.

Run No. 5: The general procedure of Example 2 was repeated. However, in this instance the TADEDS was replaced with Compound 9-C from Run No. 4 of Example 9. The results were indistinguishable from those of Example 2.

Run No. 6: The general procedure of Example 1 was repeated. However, in this instance the procedure was modified by replacing the DEDSC of Example 1 with Compound 9-B from Run No. 3 of Example 9. The product "Compound 9-C" was identified by elemental analysis, NMR, and its infrared spectrum as

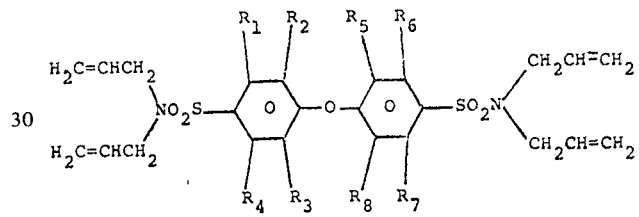

in which $R_1$ through $R_8$ were each —$CH_3$.

Run No. 7: The general procedure of Example 2 was repeated. However, in this instance the TADEDS was replaced with Compound 9-C from Run No. 6 of Example 9. The results were indistinguishable from those of Example 2.

Example 10

A series of runs was made using the general procedure of Example 5. However in each of these runs the methylene bis-aniline was replaced with an equal molar amount of one of the materials listed in Table I, below (making at least one run with each of said materials).

Table I

| Run No. | Material |
| --- | --- |
| 1 | $H_2N$—⟨O⟩—$NH_2$ |
| 2 | $H_2N$—⟨H⟩—$NH_2$ |
| 3 | $H_2N$—$CH_2$—⟨O⟩—$CH_2$—$NH_2$ |
| 4 | $H_2N$—⟨O⟩—$CH_2$—$NH_2$ |
| 5 | $H_2N$—$CH_2CH_2$—$NH_2$ |

TABLE I (Continued)

6 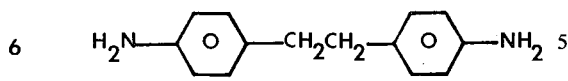

7 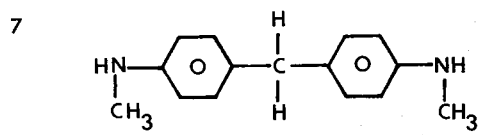

8 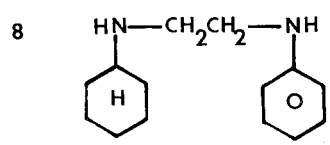

9 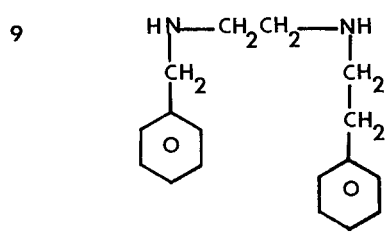

10 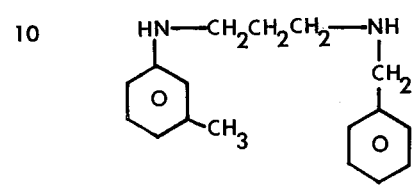

In each instance a resulting intermediate compound having the formula

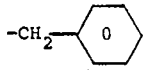

in which; (a) $R_1$ through $R_8$ were hydrogen; and (b) A was $$SO_2-\underset{R_{10}}{N}-R_9-\underset{R_{11}}{N}-O_2S$$

in which $R_9$, $R_{10}$, and $R_{11}$ were determined by the material listed in Table I used to prepare said intermediate compound which was isolated and identified by elemental analysis, NMR, and its infrared spectrum. Thus, where the material in Table I was

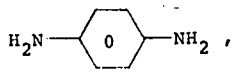

$R_9$ was phenylene and $R_{10}$ and $R_{11}$ were hydrogen and where the material in said table was

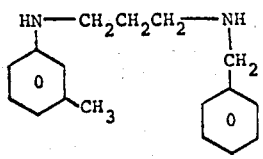

$R_9$ was —$CH_2CH_2CH_2$—, $R_{10}$ was

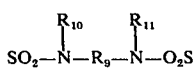

and $R_{11}$ was

In each instance the intermediate was reacted with diallylamine as in Example 5 to produce a product compound having the formula

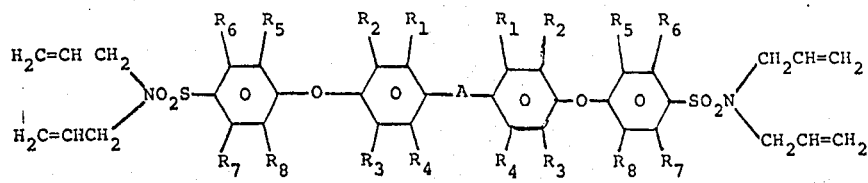

in which $R_1$ through $R_8$ were hydrogen and A, $R_9$, $R_{10}$, and $R_{11}$ were the same as in the intermediate compound from which the product compound was prepared. The intermediate and product compounds were identified by elemental analysis and by their infrared and NMR spectra.

Example 11

A series of runs were made using the general procedure of Example 4. However, in these runs the procedure was modified by replacing the TADEDS of Example 4 with the product compounds of Example 10 (using one of said product compounds in each run). In each instance the results were indistinguishable from those of Example 4.

Example 12

A number of runs were made using the general procedure of Run No. 1 of Example 9. However, in each of runs the 2,3,5,6-tetramethyl phenol was replaced with a material listed in Column A of Table II, and the 1-bromo-2,3,5,6-tetramethyl benzene was replaced with a material listed in Column B of Table II.

Table II

| Column A | Column B |
|---|---|
| 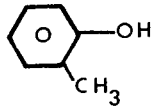 | 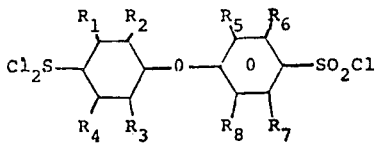 |
| 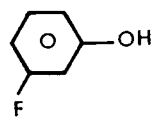 | |
| 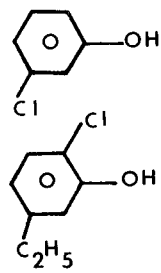 | |
| 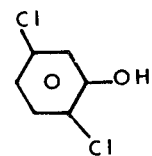 | |

In each instance the product was identified by elemental analysis, NMR, and its infrared spectrum as a compound ("Compound 12-A") having the formula

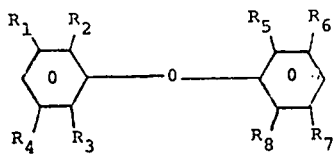

in which $R_1$, $R_2$, $R_3$, and $R_4$ corresponded to the function groups (other than —OH) of the compound (substituted phenol) selected from Column A of Table II which was used to prepare the Compound 12-A and $R_5$, $R_6$, $R_7$, and $R_8$ corresponded to the functional groups (other than bromine) of the substituted bromobenzene selected from Column B of Table II which was used to prepare the Compound 12-A.

A number of runs were made repeating the general procedure of Run No. 2 Example 9. However, in each instance, the procedure was modified by using a Compound 12-A selected from the above-prepared group of compounds which were designated Compound 12-A.

In each instance the resulting product was identified by elemental analysis, NMR, and its infrared spectrum as a compound ("Compound 12-B") having the formula

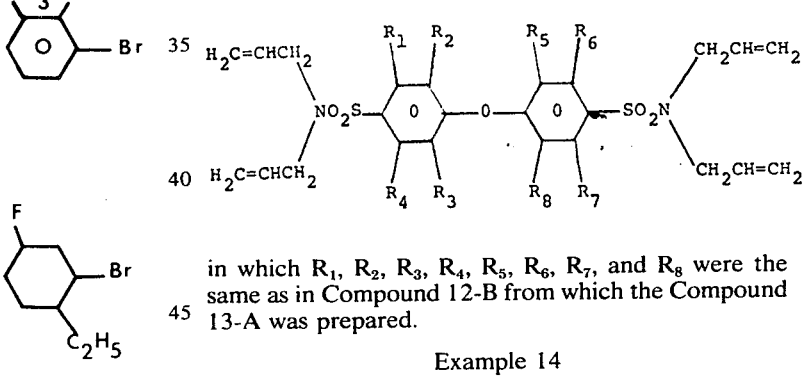

in which each of $R_1$, $R_2$, $R_3$, $R_4$, $R_5$, $R_6$, $R_7$, and $R_8$ was the same as in the Compound 12-A from which the Compound 12-B was prepared.

Example 13

The general procedure of Example 1 was repeated. However, in this instance the procedure was modified by making a series of runs in which the diphenyl ether-4,4'-disulfonyl chloride of Example 1 was replaced with a Compound 12-B from Example 12 (using one Compound 12-B in each run).

In each run the product ("Compound 13-A") was identified by elemental analysis, NMR, and its infrared spectrum as in which $R_1$, $R_2$, $R_3$, $R_4$, $R_5$, $R_6$, $R_7$, and $R_8$ were the same as in Compound 12-B from which the Compound 13-A was prepared.

Example 14

A series of runs was made using the general procedure of Example 4. However in each of these runs the procedure was modified by replacing the TADEDS with a Compound 13-A from Example 13 (using one Compound 13-A per run). In each instance the results of these runs were indistinguishable from those of Example 4.

Example 15

A series of runs was made using the general procedure of Example 5. However, in each of these runs the methylene bis-aniline was replaced (on a mole for mole basis) with one of the materials listed in Table I and in each run the DEDSC was replaced (on a mole for mole basis) with a Compound 12-B prepared according to the procedure of Example 12, supra, using one Compound 12-B in each run and making sufficient runs to insure that each Compound 12-B was reacted with each of the materials listed in said Table I.

In each instance the resulting product was identified by elemental analysis, NMR, and its infrared spectrum as a compound ("Compound 15-A") having the formula

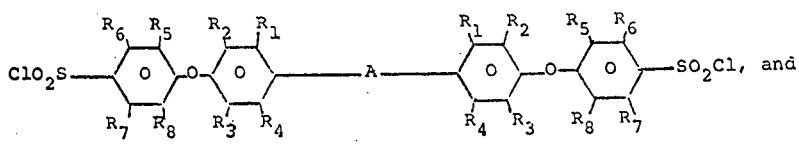

in which (a) $R_1$, $R_2$, $R_3$, $R_4$, $R_5$, $R_6$, $R_7$, and $R_8$ were as in the Compound 12-B from which the particular Compound 15-A was prepared; (b) A was

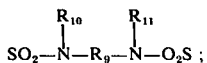

and (c) $R_9$, $R_{10}$, and $R_{11}$ were determined by the material listed in Table I from which the particular Compound 15-A was prepared. For example, where the material in Table I was

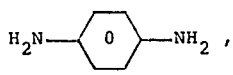

$R_9$ was phenylene and $R_{10}$ and $R_{11}$ were hydrogen and when the material in said table was

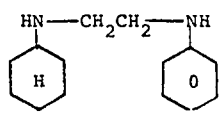

$R_9$ was —$CH_2CH_2$—, $R_{10}$ was

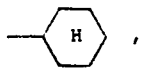

and $R_{11}$ was

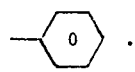

Example 16

A series of runs was made using the general procedure of Example 1. However in these runs the procedure was modified by replacing, in each instance, the DEDSC with an equal molar amount of a Compound 15-A (using one Compound 15-A in each run and making at least one run with each Compound 15-A).

In each instant the resulting product was identified by elemental analysis, NMR, and its infrared spectrum as a compound ("Compound 16-A") having the formula $R_{10}$, and $R_{11}$ are as in the particular Compound 15-A from which the particular Compound 16-A was prepared.

Example 17

A series of runs were made using the general procedure of Example 4. However in each of these runs the procedure was modified by replacing the TADEDS with an equal molar amount of a Compound 16-A. In each instance the results were indistinguishable from those obtained in Example 4.

In other runs using the general procedure of Example 4 and 17 the mole ratio of TADEDS (or the compounds recited in Embodiments B and the embodiments thereunder) to pentaerythritol tetrakis (3-mercaptopropionate) was varied over the range of 1:0.8–1.2, and excellent results were obtained in each instance.

In other runs using the general procedure of Examples 4 and 17 the pentaerythritol tetrakis (3-mercaptopropionate) was replaced with a large number of polythiols having at least two —SH groups per molecule and including ethylene glycol ($\beta$-mercaptopropionate), propylene glycol ($\beta$-mercaptopropionate), and the polythiols disclosed in U.S. Pat. No. 3,615,450 (Werber et al, 96/35.1) the equivalent ratio of —$CH_2$=$CH_2$ groups of the TADEDS or a Compound 16-A to —SH groups varied over the range of 1:0.8–1.2. In each instance the results were indistinguishable from those of Example 4.

In other runs using the general procedure of Examples 4 and 17 the benzophonone was replaced with the UV sensitizers (photoinitiators) recited in the aforesaid Werber et al patent and the amounts of said photoinitiators recited in said Werber et al patent. In each instance the results were indistinguishable from those of Examples 4 and 17.

In still other runs the general procedures of Examples 4 and 17 were repeated. However in these runs the fillers of the aforesaid Werber et al patent (in the quantities taught by said patent) were incorporated into and admixed with the mixtures of TADEDS and polythiol (or Compound 16-A and polythiol) before applying said mixtures to the laminated offset blanket carcasses. In each instance the results were indistinguishable from those of Example 4.

In other runs using the general procedure of Example 4 and Example 17 the procedure was modified by incorporating into and admixing with the mixtures of TADEDS and polythiol (or Compound 16-A and polythiol) the pigments, odor masks, light-scattering agents,

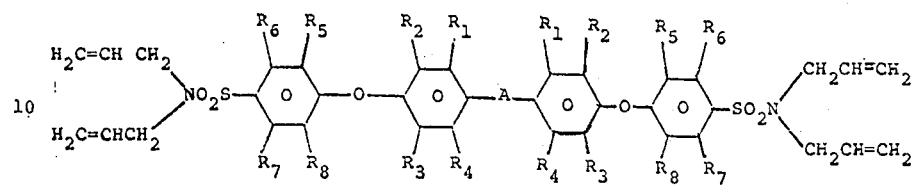

plasticizers and antioxidants of said Werber et al patent in the quantities taught by said patent. In each instance the results were substantially indistinguishable from those of Example 4.

We have found that radiation (light) having a wavelength of 2000–4000A is excellently adapted for curing compositions comprising TADEDS and a polythiol (or a Compound 16-A and a polythiol).

In another series of runs the general procedure of Examples 4 and 17 were repeated. However in each of these runs the benzophenone was omitted and the acetone solution of TADEDS and pentaerythritol tetrakis (3-mercaptopropionate) or the acetone solution of a Compound 16-A and pentaerythritol (3-mercapotpropionate) was applied to an aluminum surface and, after drying (evaporating the acetone therefrom), cured by radiation with a high energy ionizing radiation (an electron beam). The effective radiation dosage used were 0.5–30 megarads preferably 2–10 megarads. The cured coating was a hard protective coating firmly bonded to the metal.

In other instances the electron beam was replaced with; (a) an X-ray beam; and (b) a beam of neutrons. Both the X-ray beam and the beam of neutrons at dosage levels of 0.5–30 megarads gave a hard protective coating of cured polymer firmly bonded to the aluminum surface.

In another series of runs the general procedure of Examples 4 and 17 were repeated. However in each of these runs the benzophenone was omitted and the acetone solution of TADEDS and pentaerythritol tetrakis (3-mercaptopropionate) or the acetone solution of a Compound 16-A and pentaerythritol (3-mercaptopropionate) was admixed with an amount of a peroxide catalyst effective to produce crosslinking and coated onto an aluminum surface. The acetone was evaporated therefrom, and in each instance the coating cured forming a hard protective coating firmly bonded to the aluminum. Peroxides used with excellent results included cumyl peroxide, methylethylketone peroxide, 1,2-peroxycyclopentane,

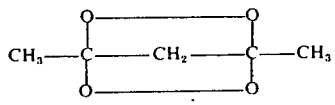

Lupersol 224 (a commercially available peroxide catalyst), and Lupersol 256 (a commercially available peroxide catalyst). In general about 2% (based on the weight of the resulting mixture (exclusive of acetone)) of peroxide catalyst was used but excellent results were obtained with larger and small amounts of catalyst.

Thus compositions comprising TADEDS and a polythiol or a Compound 16-A and a polythiol or a composition containing a compound equivalent to TADEDS and a thiol (or a composition containing a compound equivalent to any one of our above-described Compound 16-A) is a free radical curable composition. We prefer to refer to our free radical curable compositions as curable compositions. The free radicals for curing such compositions can be generated by actinic light (preferably having a wave length of ca. 200–4000A), by high energy ionizing radiation, or by a free radical generating peroxide.

As used herein, the term "lower alkyl group" means an alkyl group having 1–7 carbon atoms.

As used herein, the term "mole" has its generally accepted meaning—a mole of a substance being that quantity of the substance which contains the same number of molecules of the substance as there are atoms of carbon in 12 g of pure $^{12}C$.

As used herein, the term "g" means gram (or grams).

The term "mil", as used herein, means 0.001 inch.

The term "percent (%)", as used herein, means parts per hundred, and the term "parts" means parts by weight unless otherwise defined where used.

The term "ml" as used herein means milliliter (0.001 liter).

As applied to TADEDS or to any Compound 16-A the term "equivalent" means that quantity of TADEDS or said Compound 16-A which contains one —CH=CH$_2$ group (i.e., 27.0 g of the —CH=CH$_2$ group); ¼ mole of TADEDS or a Compound 16-A is an equivalent of TADEDS or the Compound 16-A.

As applied to a polythiol the term "equivalent" means that quantity of the polythiol which contains one —SH group (i.e., 33.1 g of —SH group); ¼ mole of pentaerythritol tetrakis (3-mercaptopropionate is an equivalent, and ⅓ mole of trimethylol-propane tris (thioglycolate) is an equivalent.

We claim:
1. A compound having the formula

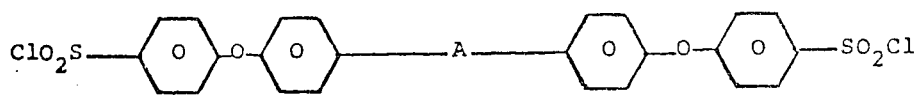

in which:
a. A is

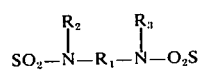

b. R$_1$ is

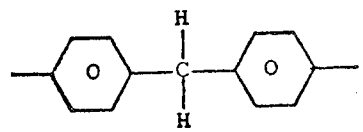

or
an alkylene group having 2–12 carbon atoms and
c. R$_2$ and R$_3$ are hydrogen.

2. The compound of claim 1 in which R$_1$ is

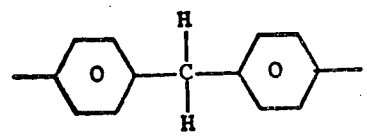

3. The compound of claim 1 in which R$_1$ is an alkylene group having 2–12 carbon atoms.

4. The compound of claim 1 in which R$_1$ is —CH$_2$(CH$_2$)$_4$CH$_2$—.

* * * * *